United States Patent [19]

Temple

[11] Patent Number: 5,421,827
[45] Date of Patent: Jun. 6, 1995

[54] FECAL INCONTINENCE DEVICE AND APPLICATOR THEREFOR

[76] Inventor: John E. Temple, 523 Wilkinson, Chelsea, Mich. 48118

[21] Appl. No.: 778,989
[22] PCT Filed: Nov. 15, 1990
[86] PCT No.: PCT/US89/01960
 § 371 Date: Nov. 7, 1991
 § 102(e) Date: Nov. 7, 1991
[87] PCT Pub. No.: WO90/13274
 PCT Pub. Date: Nov. 15, 1990
[51] Int. Cl.⁶ .............................................. A61F 5/44
[52] U.S. Cl. ........................................ 604/355; 383/67; 383/68
[58] Field of Search ........................... 4/144.1–144.3; 604/328, 332, 336, 337, 338, 341, 344, 348, 355, 15, 336; 383/33, 67, 71, 68

[56] References Cited

U.S. PATENT DOCUMENTS

| | | | |
|---|---|---|---|
| 2,448,938 | 9/1948 | Wayne | 128/285 |
| 2,564,773 | 8/1951 | Wade | 128/275 |
| 3,522,807 | 8/1970 | Millenbach | 128/283 |
| 3,804,093 | 4/1974 | Fell | 128/286 |
| 3,938,521 | 2/1976 | Ritota et al. | 604/328 |
| 4,030,500 | 6/1977 | Ronnquist | 604/328 |
| 4,067,335 | 1/1978 | Silvanov | 604/328 |
| 4,182,332 | 1/1980 | Delaney | 604/328 |
| 4,210,131 | 7/1980 | Perlin | 604/328 X |
| 4,253,460 | 3/1981 | Chen et al. | 128/283 |
| 4,368,733 | 1/1983 | Sanidas | 604/355 |
| 4,445,898 | 5/1984 | Jensen | 604/337 |
| 4,496,356 | 1/1985 | Lognion | 604/328 |
| 4,534,768 | 8/1985 | Osburn et al. | 604/355 X |
| 4,536,178 | 8/1985 | Lichstein et al. | 604/15 |
| 4,553,969 | 11/1985 | Taylor | 604/355 |
| 4,611,350 | 9/1986 | Kaczerwaski | 383/71 X |
| 4,650,817 | 3/1987 | Allen, Jr. et al. | 523/105 |
| 4,755,177 | 7/1988 | Hill | 604/336 |
| 4,784,656 | 11/1988 | Christian | 604/332 X |
| 4,850,986 | 7/1989 | Temple | 604/332 X |
| 4,986,822 | 1/1991 | Anderson | 604/355 X |

*Primary Examiner*—Randall L. Green
*Assistant Examiner*—Mary Beth Jones
*Attorney, Agent, or Firm*—Young, MacFarlane & Wood

[57] ABSTRACT

An incontinence device comprising a generally tubular soft latex shape (20) open at both ends. The upper end (24) is smoothly curved and tapered inward (28) to the opening (26) with the latex of minimal thickness and coated on the outside adjacent the opening (26) with a suitable adhesive for contact with the skin about the anal opening. The lower end (22) is partially folded and clipped to permit the device to be affixed with an applicator (30) specifically shaped (32) for the purpose and inserted within the device. The shape and material of the device permits the device to fully stretch and shrink with the anal opening while remaining adhesively affixed to the skin. An extended polyvinyl chloride/urethane mixture of similar elasticity, flexibility and elongation may be substituted for the latex. Because of the very thin wall thickness, the device may be formed as a fiat hollow body (120) which expands in use. The applicator (430) may be permanently attached to the device and formed to serve as a vent (433) for liquids as further alternative constructions.

9 Claims, 7 Drawing Sheets

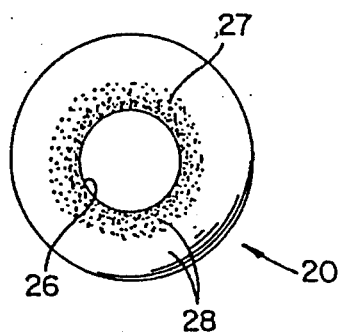
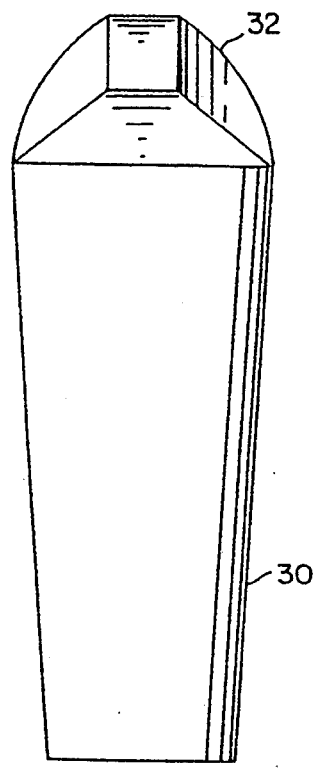
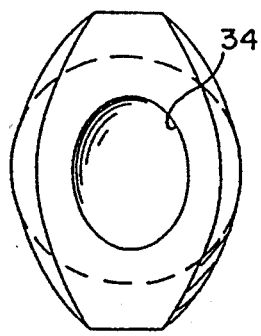
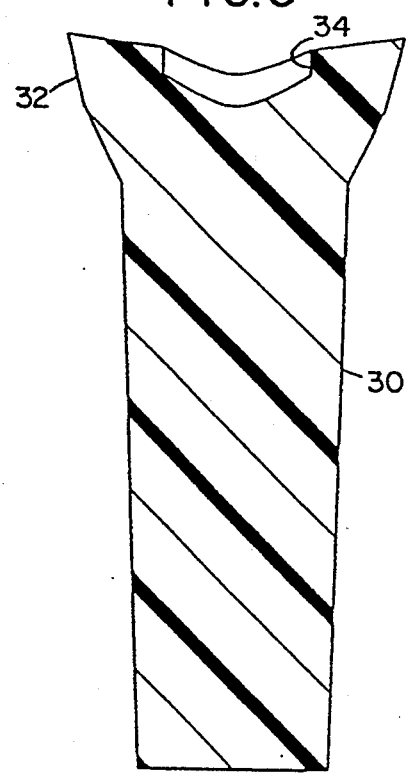
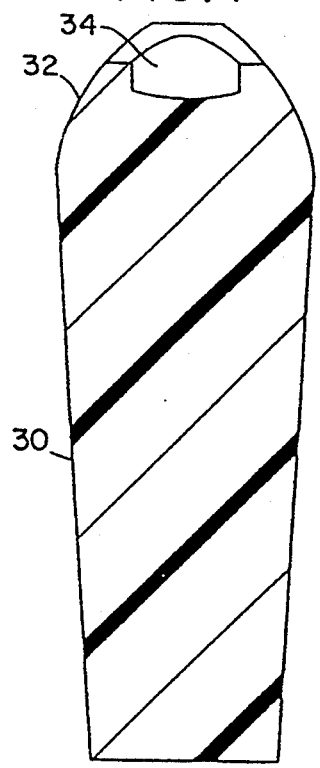

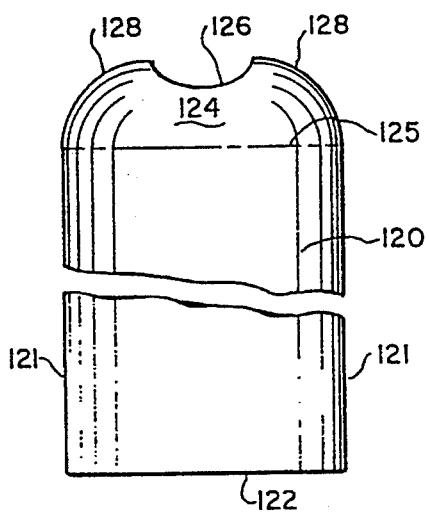
FIG. 12a
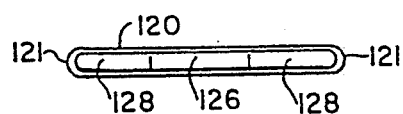
FIG. 12b
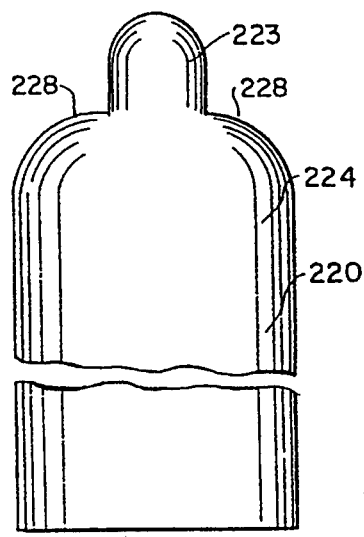
FIG. 13a
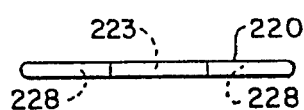
FIG. 13b
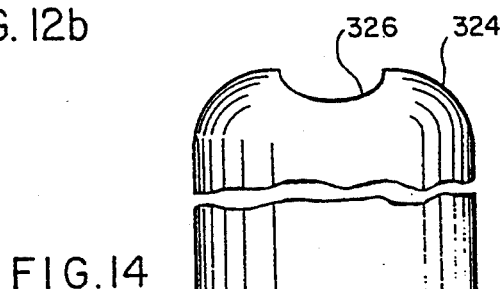
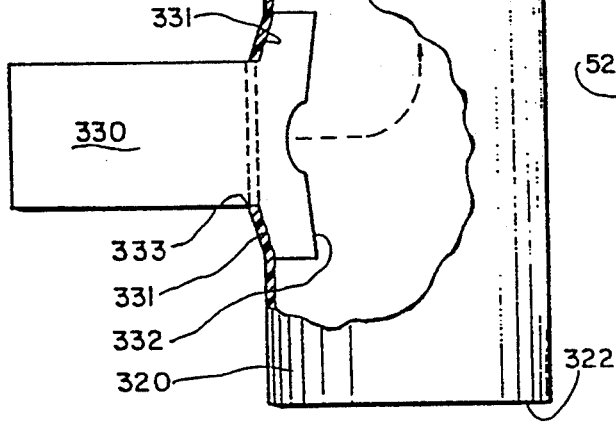
FIG. 14
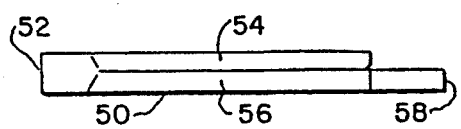
FIG. 15b
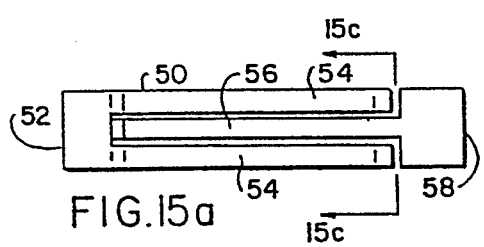
FIG. 15a
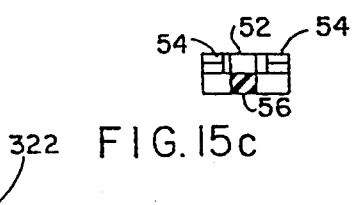
FIG. 15c

FECAL INCONTINENCE DEVICE AND APPLICATOR THEREFOR

BACKGROUND OF THE INVENTION

The field of the invention pertains to medical appliances and, in particular, to devices that can be attached to the exterior skin of a person about or in an opening with the purpose of accepting and containing any solid or liquid material flowing from the opening. Such devices require a means of attachment that does not damage the skin but is reasonably secure.

Lognion, U.S. Pat. No. 4,496,356, discloses an anal excretion collecting rectal catheter that is Insertable beneath the sphincter muscles about the opening. The Lognlon device comprises a collecting tube open at one end with a resilient ring that fits within the rectal opening.

Wade, U.S. Pat. No. 2,564,773, discloses a therapeutic agent comprising a thimble and latex bag insertable into a bodily opening for the collection of fluids. The bag folds within the thimble before use and may be attached to the thimble with an adhesive. The thimble includes an opening for the admission of fluids and Is directly insertable into the bodily opening.

Wayne, U.S. Pat. No. 2,448,938 and Swiss Pat. No. 113 453 each disclose a sanitary protective appliance of similar structure to receive bodily fluids and semi-solids from infections and incisions. The appliances comprise soft thin rubber tubes of accordion like shape with an opening of relatively large diameter. On the inside surface adjacent the opening is an adhesive ring to enable the device to be adhesively attached to the skin about the body opening from which there is a discharge.

Chen et al., U.S. Pat. No. 4,253,460 and Allen, Jr. et al., U.S. Pat. No. 4,650,817 both disclose adhesives suitable for attaching appliances such as ostomy devices to the skin about a body opening. Such adhesives must be secure, reasonably fluid tight but nevertheless easy to remove without damage to the skin.

U.S. Pat. No. 3,522,807 discloses an incontinence bag that has a pleated arrangement about the anus to expand and contract with the opening and closing of the anus. The overlapping leaves of the pleats do not provide for complete adhesive attachment to the skin thus permitting leakage and providing a difficult attachment.

U.S. Pat. No. 4,445,898 discloses a foam backed skin barrier attachment and incontinence bag. The skin barrier is disclosed as soft, pliable, stretchable and contractable foam backed plastic 0.080 to 0.400 inches thick. Plastic backed by foam has limited stretchability of less than 25% which limits the expandability of the anal hole in the skin barrier to an amount less than needed for most patients, in such cases, the anus can not open sufficiently thereby causing severe pain or the adhesive fails and the bag detaches and leaks.

Devices insertable within body openings have been found to cause permanent damage to the sphincter muscles after prolonged use. With a view toward overcoming and avoiding damage to the sphincter muscles of the anal opening but nevertheless providing a secure receptacle for bodily waste that does not damage the skin surrounding the anus, is sufficiently elastic (an elastic limit of about 200% or more) to accomodate the full opening of the anus and is easy to install the following described incontinence device has been developed.

SUMMARY OF THE INVENTION

The incontinence device comprises a generally tubular soft latex shape, tube or bag open at both ends but having a clip to retain the lower end partially folded up and closed. The upper end of the device is curved and tapered inward to the opening with the latex of minimal thickness, preferably 0.003 to 0.006 inches (0.076 to 0.152 millimeters), and coated on the outside with a suitable adhesive for contact with the skin about the anal opening. The latex is purposefully made as thin as possible to enable the latex to offer little or no resistance to stretching with the skin as the anus is fully opened and closed by the sphincter muscles. Soft latex of the above thickness has a better than 400% elastic limit.

A specifically shaped applicator is provided to enable a nurse or physician to easily apply the adhesive to the device and to conveniently and securely attach the adhesive and latex about the upper opening to the skin about the anus. The applicator fits within the tube and is removed through the lower end of the tube. The clipped lower end also permits the tube to be periodically opened to permit gases accumulated therein to be expelled, or fecal matter to be removed and the bag to remain on the patient.

In an alternate version of the device, the device is formed of latex or an extended polyvinyl chloride/urethane mixture of similar elastic limit. The device is initially manufactured as a substantially flat hollow tube. Because of the extreme thinness of the device wall thickness, the hollow tube can expand into a substantially round tube as needed.

The applicator in alternative embodiments may be permanently attached to the device and also serve as a vent for liquids. In this construction the applicator is permanently mounted in the sidewall of the device and may or may not penetrate the wall. If the liquid vent is included then the applicator is located near the bottom of the device and penetrates the wall. Gases and liquids can be vented and when the device is filled with fecal matter it can be disposed conveniently. Such a combination simplifies the use of the device and eliminates the possibility of a non-sterile or contaminated applicator being improperly reused.

DESCRIPTION OF THE DRAWINGS

FIG. 2 is an upper end view of the device;
FIG. 4 is an elevator view of the applicator;
FIG. 5 is a top view of the applicator;
FIG. 6 is a cross-section of the applicator taken along the line 6—6 of FIG. 3;
FIG. 7 is a cross-section of the applicator taken along the line 7—7 of FIG. 3;
FIG. 8 is a cross-section of the applicator taken along the line 8—8 of FIG. 3;
FIGS. 12 illustrates in side and bottom view an alternate flat form of the device;
FIG. 13 illustrates in side and bottom view a dipping tool to make the alternate flat form of FIG. 12;
FIG. 14 is a cutaway side view of the device having the applicator permanently attached;

FIGS. 15 illustrates a closure clamp for the device in plan view, side view and end view respectively;

DESCRIPTION OF THE PREFERRED EMBODIMENTS

Figure 1:
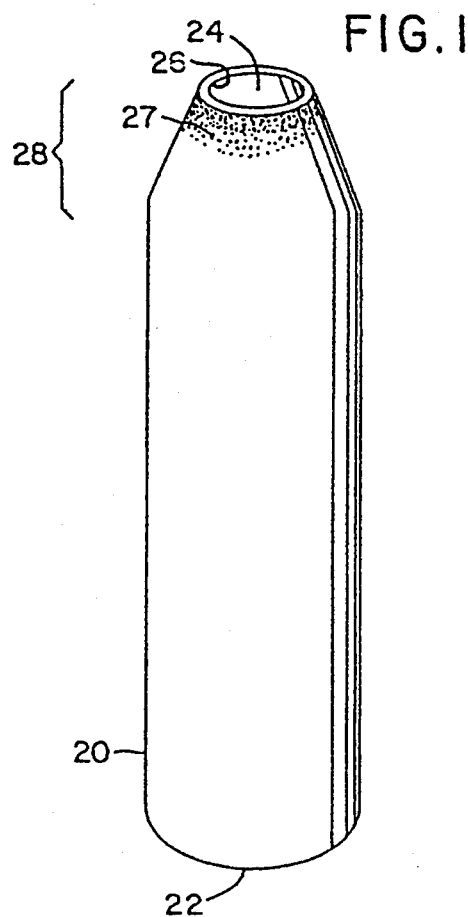
FIG. 1 is a perspective view of the device.

Illustrated in FIGS. 1 and 2 is a generally tubular shape 20 formed of soft latex or a similar material that is liquid impermeable, very flexible and soft to the skin. The lower end 22 is open. As illustrated below the lower end may be closed by folding over and retaining with a plastic closure clip (not shown). The device is suitably about 18 inches long and 3 inches in diameter. With the exception of the upper end 24 a wall thickness of about 0.010 to 0.0020 inches (0.254 to 0.051 millimeters) is suitable.

The upper end 24 includes an opening 26 of about one and one-quarter inches in diameter surrounded by an upper curved generally conical portion 28 extending down to the tubular shape 20. The curved upper portion 28 is made specifically very thin for maximum elasticity and flexibility and adjacent the opening 26 is coated on the outside 27 just prior to use with an adhesive suitable for secure attachment to the skin.

Since the human skin about the anal opening stretches and contracts a substantial amount with opening and closing of the anal sphincter muscles, the conical portion 28 must also stretch and contract with minimal resistance and maximum flexibility to prevent chafing of the skin and failure of the adhesive attachment. A thickness of 0.003 to 0.006 inches (0.076 to 0.152 millimeters) for soft latex has been found preferable with a two part adhesive comprising polyolmethylsiloxane in trichlorotriflouroethane. Thicknesses of about 0.015 inches (0.381 millimeters) for the latex adjacent the upper opening have been found too inflexible for satisfactory use although a thickness of less than 0.010 inches (0.254 millimeters) is serviceable. The thinned latex has been found far superior to most film plastics by providing elasticity on the order of 400%, or more. Latex of 0.001 inches (0.0254 millimeters) provides additional flexibility, however, the minimal thickness is more difficult to manufacture. A plastic material recently available ("KRATON TM, Shell Chemical Company, Houston, Tex., U.S.A.) at thicknesses similar to the latex or less has adequate elongation (400%) and appears to be a possible option but requires greater force to provide the elongation.

The inside of the device is preferably coated with a powder to prevent the sticking of stools to the inside of the latex tube. Cornstarch, baby powder or medical grade silicone lubricant are suitable materials.

Figure 9:
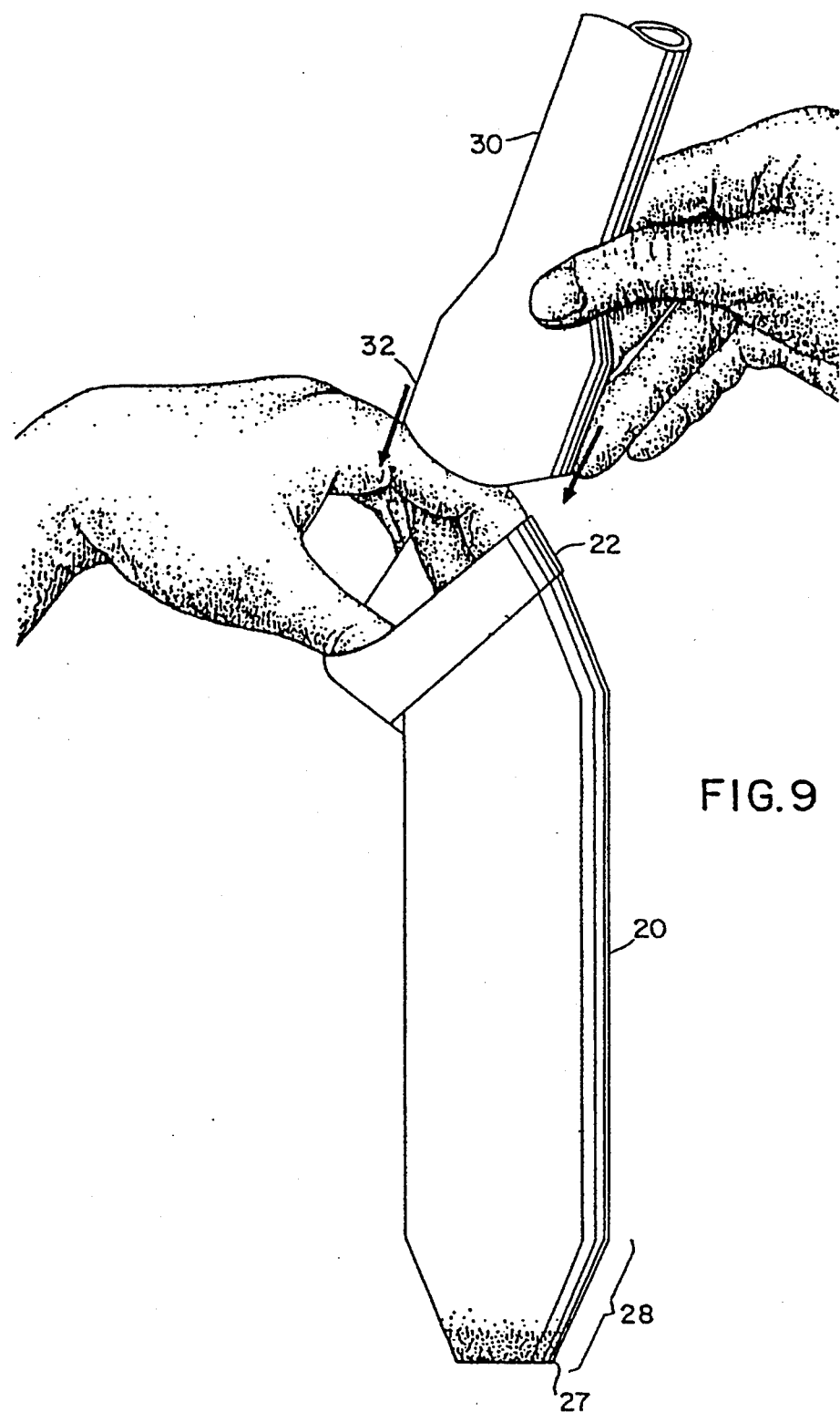
FIG. 9 illustrates insertion of the applicator into the device.

Illustrated in FIGS. 3 through 8 is an applicator comprising a handle portion 30 and shaped top 32. As shown the top 32 is generally saddle shaped with a depressed oval center 34. The saddle shape 32 is specifically to fit the skin and muscle structure about the human male or female anus. The saddle shape 32 is sized to fit within the conical portion 28 of the device. More particularly, the conical portion 28 is stretched over the applicator saddle shape 32 after insertion of the applicator from the open lower end 22 as shown in FIG. 9.

Figure 10:
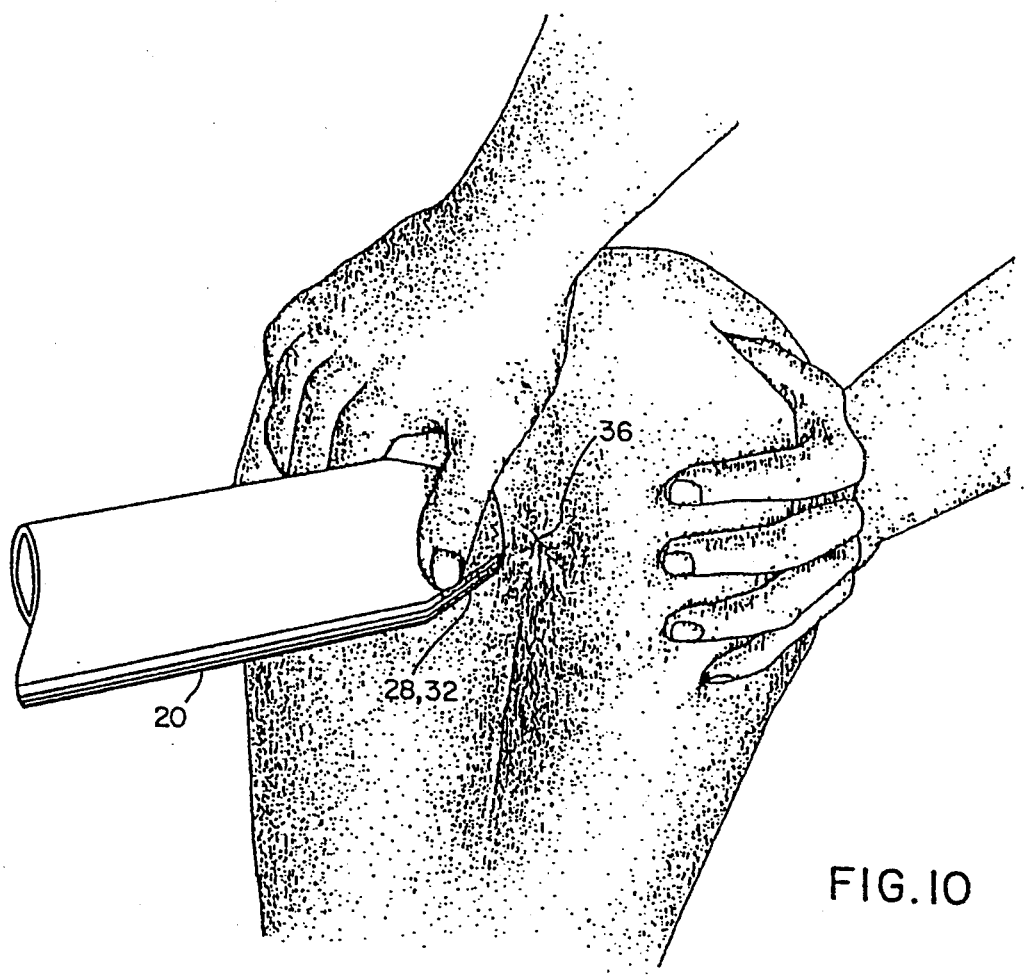
FIG. 10 illustrates attachment of the device.
Figure 11:
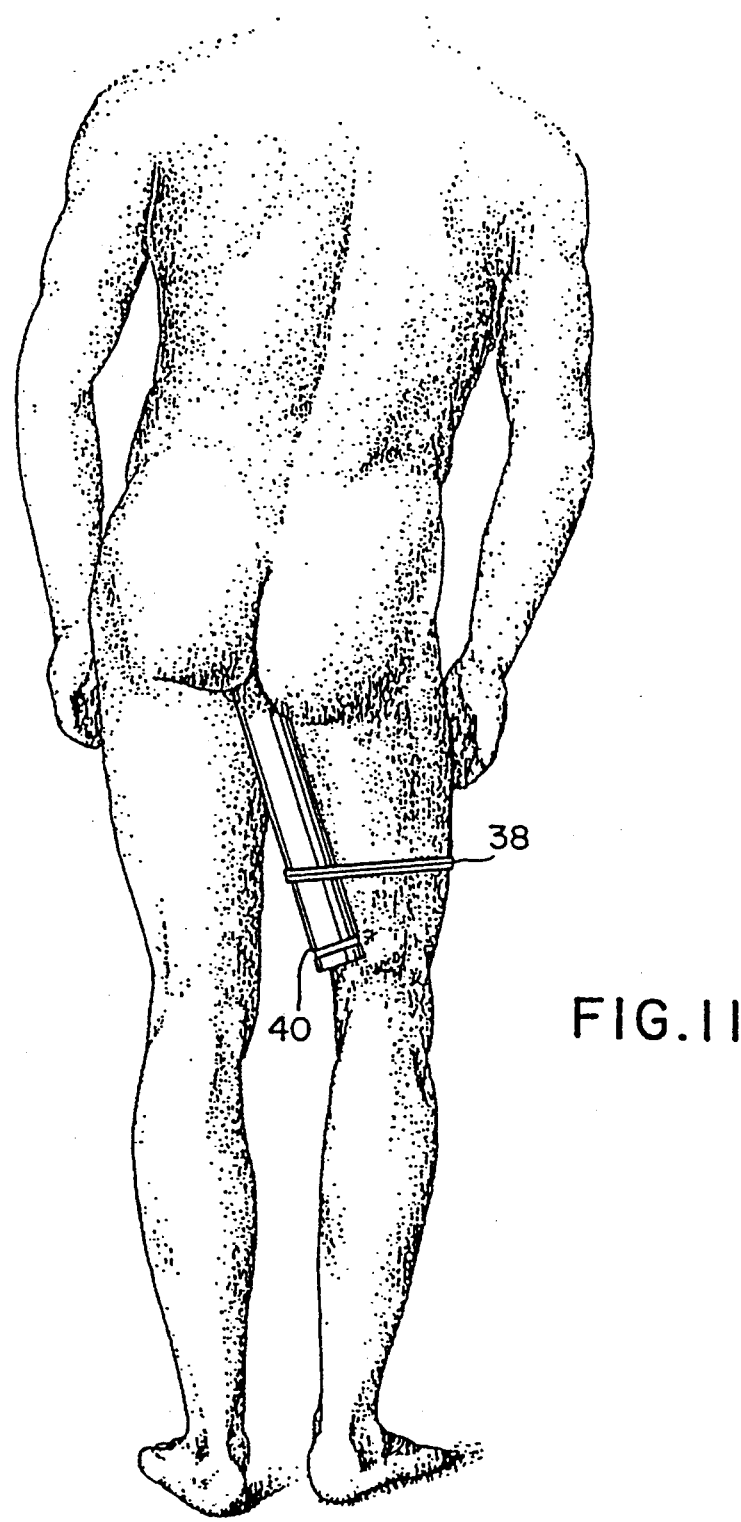
FIG. 11 illustrates the device in place.

As best shown in FIG. 10, the device 20 with the applicator held thereinside and the conical portion 28 stretched smoothly over the saddle shape 32 is spray coated with adhesive and applied about the anus 36. In place as shown in FIG. 11 the device may be lightly taped at 38 to the thigh and folded and clipped at 40.

In FIGS. 12a and 12b an alternate form of the incontinence device is illustrated in its as manufactured shape. Whereas the first embodiment shown in FIG. 1 is manufactured on a substantially cylindrical mandrel tapered toward the top, the alternate form of FIGS. 12a and 12b is formed flat as further described below.

As shown in FIGS. 12a and 12b the device comprises a hollow flat tube 120 constructed of soft latex or a plastic having the required elasticity or elongation such as a recently developed composite of extended polyvinyl chloride/urethane. The bottom end 122 of the tube 120 is open. The upper end 124 is edgewise curvedly tapered 128 toward an opening 126 into the interior of the device.

The material thickness over the curvedly tapered portion 128 must be sufficiently thin to provide the flexibility, elasticity and elongation sufficient to substantially equal or exceed that of the human skin over the anus. A suitable thickness range is 0.0015 to 0.0045 inches (0.0381 to 0.0114 millimeters) for the curvedly tapered portion 128 over the entire upper end 124 (above the ghosted line 125) on both sides. The major portion of the device below the line 125 may be thicker as desired and preferably is about 0.003 to 0.020 inches (0.076 to 0.508 millimeters) in thickness.

Illustrated in FIGS. 13a and 13b is a mandrel or dipping tool to form the incontinence device or bag of FIGS. 12a and 12b. A suitable material is buffed aluminum plate ⅛ inches (about 3 millimeters) in thickness and formed with a straight portion 220 and curvedly tapered portion 228 at the upper end 224. A tongue 223 extends from the upper end 224 from which the mandrel can be suspended for dipping into the latex bath or liquid plastic.

The mandrel is lowered into the bath and then slowly withdrawn. The thickness of the latex or plastic is determined by the time in the bath; therefore, the mandrel is first relatively quickly and evenly partially withdrawn upon creation of the exceptionally thin upper end 124 of the incontinence device or bag. The mandrel is then subsequently fully withdrawn upon formation of the thicker body 120 of the device.

After drying, curing and stripping from the mandrel, the opening 126 in the upper end 124 is die cut through the upper end as the device lies flat.

Illustrated in FIG. 14 is a modified incontinence device wherein the handle 330 of the applicator extends through the tubular wall 320 of the device. The saddle shaped top 332 of the applicator is located within the tubular wall 320 and the wall adhesively attached to the underside 331 of the top 332. Thus, the aperture 333 in the wall 320 for the applicator handle 330 is sealed to prevent leakage. With this embodiment the applicator head 332 is permanently inside the device and the upper end 324 can be stretched over the head 332 as in the embodiments disclosed above. However, with this embodiment the applicator is disposable with the device thereby eliminating the likelihood of reuse and contamination from reuse. As a further alternative the entire applicator may be adhesively attached within the device and either grasped through the open lower end 322 or by grasping the device about the handle.

In these embodiments of FIG. 14 the applicator should be located in the lower one-third of the device for reasons of comfort to the patient and so as not to impede the movement of solid fecal matter into the device.

Illustrated in FIGS. 15a, 15b and 15c is a clip for releasably sealing the lower end of the incontinence devices described above. The clip comprises a three pronged body 50 having a common end 52, two substantially identical side prongs 54 and a central prong 56. As shown the central prong 56 is displaced vertically from the side prongs 54 and includes grasping means 58 similar to the common end 52 which also serves as a grasping means.

To use, the clip is slid over the lower end of the device after the lower end is flattened. The central prong 56 is to one side and the side prongs 54 are to the other side. The clip may then be rolled up several turns and taped.

Figure 16A:
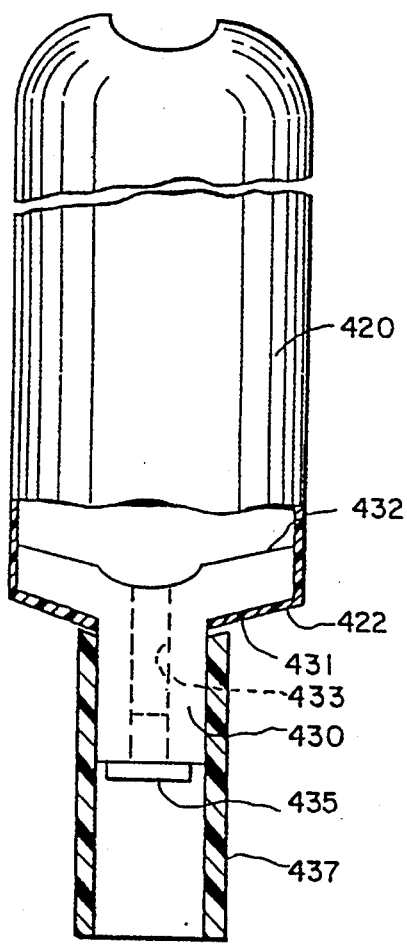
FIG. 16 illustrates cutaway side and edge views of the device having the applicator permanently attached at the lower end and fitted with a drainage vent.
Figure 16B:
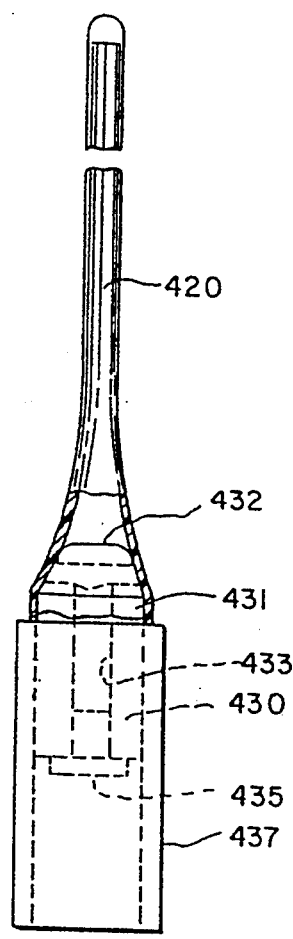

Illustrated in FIG. 16 is a further modification of the device or bag wherein the applicator head 432 is located within the lower end 422 of the device. The handle 430 of the applicator extends below the device and the underside 431 of the applicator is adhesively attached to the device about the lower end 422 to seal the lower end. The handle 430 with extension 437 and head 432 are pierced by a drain hole 433 fitted with a removable cap 435 for release of gases and liquids. This version of the device and applicator obviates the need for clipping or sealing the lower end of the bag and requires the applicator be disposed with the bag.

Figure 3:
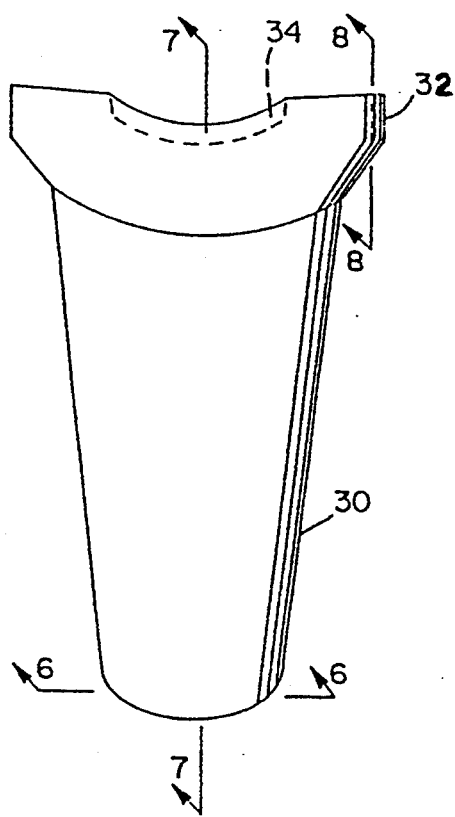
FIG. 3 is a perspective view of the applicator.
Figure 17:
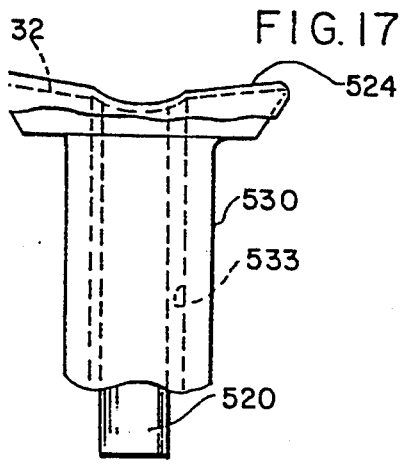
FIG. 17 illustrates an applicator with a central aperture through which extends the device.

The devices illustrated above whether formed in the substantially round tubular form shown in FIG. 1 or the substantially flat tubular form shown in FIG. 12 can easily be stretched over the saddle shaped applicator head shown in FIG. 3. Or either form of the device can be manufactured with the saddle shaped applicator therein as shown in FIGS. 14 and 16. The versatility arises from the extreme flexibility and elongation of the very thin latex or plastic material of the device. Or, the device can be threaded through an aperture 533 in the applicator handle 530 shown in FIG. 17. As above the upper end 524 of the device 520 is stretched over the upper end 532 of the applicator. In this embodiment the device may be turned inside out before threading through the aperture 533.

Figure 18A:
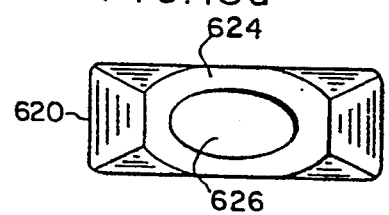
FIG. 18 illustrates a device molded to fit the applicator with minimal stretching.
Figure 18B:
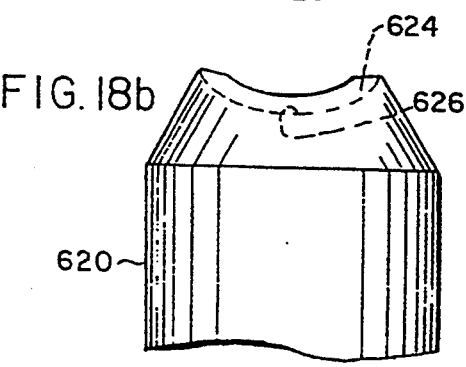

The device may alternatively be constructed of two thin flat sheets of latex or plastic solvent bonded or adhesively adhered along two edges 121 in FIGS. 12a and 12b to form a tube and across one end to form the upper end 128. The upper opening 126 is then cut as above in the final step of manufacturing the dipped form of the device. Or, the device 620 may be mandrel or injection molded to the shape illustrated in FIGS. 18a and 18b wherein the upper end 624 is shaped to conform with the applicator top with minimal stretching and the hole 626 formed in the depression.

The applicator may be made of a variety of materials both hard and flexible. A hard plastic or metal applicator forces the patient's rectal area to take the shape of the applicator. A softer applicator allows the rectal area and applicator to have some deformation. The preferable construction is a soft rubber, silicone rubber or closed cell dense foam that skins over in manufacture to provide a smooth surface.

The material chosen is preferably less than 35 Durometer and may be attached as a layer on the head of a harder plastic applicator. Or the entire applicator may be formed of an air filled polyvinyl chloride foam that skins over to provide a smooth resilient surface. A new plastic on the market (SANTOPRENE TM, Monsanto Corporation, St. Louis, Miss., U.S.A.) simulates many characteristics of natural rubber in feel and Durometer. A further advantage is the thermoplastic character permitting easier processing and scrap recycling.

I claim:

1. An incontinence device comprising a thin-walled substantially flat hollow shape (120), an opening (126) in an upper end of the flat hollow shape, said opening of substantially less area than a cross-sectional area of the flat-hollow shape, said flat-hollow shape curvedly tapering (128) to said opening, said thin-walled flat-hollow shape adjacent (124) said opening (126) configured to attach adhesively to skin externally around a patient's anus and said thin-walled shape adjacent said opening having an elongation and elasticity substantially equal to or greater than the skin externally around the anal sphincter so as to expand and contract with skin attached thereto without hindering the normal expansion and contraction of the skin externally about the anal sphincter during the passage of fecal matter, an adhesive suitable for application to an outside surface of the thin-walled flat-hollow shape adjacent (124) the opening (126) just prior to attachment to the skin, and a bottom opening (122) and a clip (50), said clip including means to grasp and seal (54,56) the bottom opening, wherein said bag has a wall thickness of between 0.010 and 0.002 inches and tapers to a wall thickness of between 0.015 to 0.0045 inches adjacent said opening.

2. The incontinence device of claim 1 comprising an elastic material dip molded on a substantially flat mandrel (220).

3. The incontinence device of claim 1 wherein said device is formed of a material of two sheets (120) of an elastic material, the sheets being bonded together along two side edges (121) and curved portions (128) thereof, thereby leaving said opening (126) unbounded.

4. A combined incontinence bag and applicator comprising a hollow membranous shape (320) having an upper portion (324) and a sidewall (320), an opening (326) in the upper portion of the membranous shape, a relatively rigid applicator permanently attached (331) to the sidewall at a distance from the upper portion of the bag, said applicator having means (332) on a first end of the applicator shaped to firmly apply the upper portion of the bag tightly against akin about a patient's anus and means (330) on a second end for grasping the applicator and moving the applicator into position against the upper portion of the bag and the skin.

5. The combined incontinence bag and applicator of claim 4 wherein the means for grasping (330) extends through the sidewall (320) of the bag.

6. The combined incontinence bag and applicator of claim 12 wherein at least a portion (430) of the applicator opens through the sidewall (420) of the bag, said portion of the applicator open through the sidewall including means (433) to vent fluids from the bag.

7. The combined incontinence bag and applicator of claim 6 wherein the means (433) to vent fluid opens from a bottom (422) of the bag.

8. An applicator in combination with hollow thin-walled incontinence bag (120), the bag being adhesively attachable to skin about an anus of a patient, comprising means (32) on a first end of the applicator shaped to firmly apply an adhesively attachable portion of the bag tightly against the skin about the anus and means (30) on a second end for grasping the applicator and applying the bag with the applicator, wherein the applicator (330) is permanently attached (331) to the incontinence bag (320).

9. The applicator of claim 8 wherein the applicator (330) is attached (331) to a sidewall (320) of the incontinence bag at a distance form the adhesively attachable portion (324) of the bag.

* * * * *

UNITED STATES PATENT AND TRADEMARK OFFICE
CERTIFICATE OF CORRECTION

PATENT NO. : 5,421,827
DATED : June 6, 1995
INVENTOR(S) : John E. Temple

It is certified that error appears in the above-indentified patent and that said Letters Patent is hereby corrected as shown below:

Column 6, line 34, claim 1, after "between" delete "0.015" and insert —0.0015—

Column 6, line 52, claim 4, after "against" delete "akin" and insert —skin—.

Column 6, line 60, claim 6, after "Claim" delete "12" and insert —4—.

Column 6, line 67, claim 8, after "with" insert —a—.

Column 8, line 5, claim 9, after "distance" delete "form" and insert —from—.

Signed and Sealed this

Sixth Day of August, 1996

Attest:

BRUCE LEHMAN

Attesting Officer

Commissioner of Patents and Trademarks